United States Patent [19]

Nemir

[11] Patent Number: 4,995,404

[45] Date of Patent: Feb. 26, 1991

[54] APPARATUS FOR TREATING BRUXISM

[76] Inventor: David C. Nemir, 1221 Baltimore Dr., El Paso, Tex. 79902

[21] Appl. No.: 236,455

[22] Filed: Aug. 25, 1988

[51] Int. Cl.⁵ .............................................. A61B 5/103
[52] U.S. Cl. .................................... 128/777; 128/782
[58] Field of Search ..................... 128/774, 776–777, 128/782, 903, 905, 733, 787; 340/573, 575

[56] References Cited

U.S. PATENT DOCUMENTS

| | | |
|---|---|---|
| 3,297,021 | 1/1967 | Davis et al. |
| 4,034,476 | 7/1977 | Johnson . |
| 4,112,926 | 9/1978 | Schulman et al. ................ 128/782 |
| 4,114,612 | 9/1978 | Benjamin . |
| 4,169,473 | 10/1979 | Samelson . |
| 4,220,142 | 9/1980 | Rosen et al. . |
| 4,304,227 | 12/1981 | Samelson . |
| 4,310,002 | 1/1982 | Takinishi et al. ............. 128/777 X |
| 4,355,645 | 10/1982 | Mitani et al. ..................... 128/777 |
| 4,390,028 | 6/1983 | Okano et al. ..................... 128/777 |
| 4,669,477 | 6/1987 | Ober ..................................... 128/421 |
| 4,734,034 | 3/1988 | Maness et al. ................. 128/777 X |
| 4,838,283 | 6/1989 | Lee, Jr. ............................... 128/777 |

Primary Examiner—Max Hindenburg
Attorney, Agent, or Firm—Deborah A. Peacock; Robert W. Weig

[57] ABSTRACT

The disclosure is directed to apparatuses for the treatment of bruxism, utilizing aversive conditioning. The apparatus provides biting surfaces and is fittable within a user's mouth. When the user bites on the biting surfaces, an electric shock is delivered. In another embodiment, an alarm is provided for arousing or alerting the user. The apparatus can determine the number of bruxing events and/or the biting force of the user. Strain gage and pressure sensing resistor (PSR) using embodiments are also disclosed.

33 Claims, 3 Drawing Sheets

APPARATUS FOR TREATING BRUXISM

FIELD OF THE INVENTION

The invention relates to the field of bruxism treatment, and more particularly to an apparatus for aversive conditioning for sufferers of bruxism.

BACKGROUND OF THE INVENTION

Bruxism is the nonfunctional gnashing, clenching or grinding of the teeth. Bruxism has been shown to cause or contribute to occlusal tooth wear, increased tooth mobility, tooth loss, bone loss, periodontal disease, muscle pain and spasm. headaches, backaches and temporomandibular joint (TMJ) dysfunction. It can occur nocturnally or diurnally but it is generally believed that this distinction represents two distinct phenomena. Nocturnal bruxism is by far the most serious and difficult to treat since the sufferer is asleep and unaware of grinding behavior.

In order to effectively treat nocturnal bruxism, it is important to understand how and when a bruxing behavior occurs during sleep. Nocturnal bruxism comprises regular repetitive side-to-side tooth contact, which differs markedly from more random patterns which occur during mastication or chewing and swallowing. Bruxism occurs during the lighter stages of sleep, primarily in stage 2 sleep. The termination of bruxism incidents is usually followed by a sleep stage lighter than that before the episodes occurred and never by a deeper sleep stage. Studies have led many researchers to hypothesize that bruxism is a disorder of arousal occurring during the transition from stages 3 and 4 of sleep, to stages 1 and 2.

A number of different treatments for bruxism have been proposed. These treatments include occlusal adjustment (see A. G. Glaros and S. M. Rao, "Bruxism: a Critical Review," *Psychological Bulletin*, vol. 84, pp. 767-781, 1977; and J. Ahlgren, K. A. Omnell, B. Sonesson and N. G. Toremalm, "Bruxism and Hypertrophy of the Masseter Muscle," *Practica Oto-Rhino-Laryngologica*, vol. 31, pp. 22-29, 1969); the use of occlusal appliances, such as night guards, and occlusal splints (see Glaros, et al., above) and J. E. Mejias, and N. R. Mehta, "Subjective and Objective Evaluation of Bruxing Patients Undergoing Short-Term Splint Therapy." *Journal of Oral Rehabilitation*, vol. 9, pp. 279-289, 1982, medication, such as local anesthesia or tranquilizers (see A. I. Chasins, "Methocarbamal (Robaxin) as an Adjunct in the Treatment of Bruxism," *Journal of Dental Medicine*, vol. 14, pp. 166-178, 1959; and M. A. Goldstein, "Clinical Investigation of Mephate in Dentistry," *Dental Digest*, vol. 62, p. 454, 1956); massed negative practice (e.g., clenching the teeth while awake to fatigue the jaw muscle) (see W. A. Ayer, "Massed Practice Exercises for the Elimination of Tooth-Grinding Habits," *Behavior Research and Therapy*, vol. 14, pp. 163-164; 1976; R. F. Heller and A. Forgione, "An Evaluation of Bruxism Control: Massed Negative Practice and Automated Relaxation Training," *Journal of Dental Research*, vol. 54, pp. 1120-1123, 1975); relaxation therapy (see B. A. Brown, *Stress and the Art of Biofeedback*, Harper and Row, New York, pp. 82-85, 1977; R. Hamilton, "Battling Bruxism through Biofeedback," *TIC*, pp. 8-11, May 1986; Heller and Forgione, above; and V. Cornellier, D. M. Keenan and K. Wisser, "The Effects of EMG Biofeedback Training upon Nocturnal and Diurnal Bruxing Responses," *International Journal of Orofacial Myology*, vol. 8, pp. 11-15, 1982); and aversive conditioning (see W. J. DeRissi, "A Conditioning Approach to the Treatment of Bruxism," PhD Thesis, University of Utah, 1970; R. F. Heller and H. R. Strang, "Controlling Bruxism Through Biofeedback," *Behavior Research and Therapy*, vol. 11, pp. 327-329, 1973; R. A. Moss, D. Hammer, H. E. Adams, J. O. Jenkins, K. Thompson and J. Haber, "A More Efficient Biofeedback Procedure for the Treatment of Nocturnal Bruxism," *Journal of Oral Rehabilitation*, vol. 9, pp. 125-131, 1982; G. T. Clark, P. Beemsterboer and J. D. Rugh, "The Treatment of Nocturnal Bruxism using Contingent EMG Feedback with an Arousal Task," *Behavior Research and Therapy*, vol. 19, pp. 451-455, 1981; A. Piccione, T. J. Coates, J. M. George, D. Rosenthal and P. Karzmark, "Nocturnal Feedback for Nocturnal Bruxism, " *Biofeedback and Self Regulation*, vol. 7, pp. 405-419, 1982; and M. Cherasia and L. Parks, "Suggestions for the Use of Behavioral Measures in Treating Bruxism." *Psychological Reports*, vol. 58, pp. 719-722, 1986). Occlusal adjustment and the use of night guards represent dental approaches to treatment and are the outgrowths of mechanical etiology theories. The approach is to eliminate the trigger factors leading to bruxism and to prevent further damage to teeth and soft tissues. Relaxation therapy and medication address the stress that can lead to bruxism, whereas massed negative practice and aversive conditioning are techniques for "unlearning" bruxism behavior. Although varying degrees of success have been reported with all six treatment procedures, aversive conditioning appears to have the most promise.

Because aversive conditioning has been used with great success in treating nocturnal enuresis (bedwetting), whereby a loud buzzer responds as soon as a specially constructed bed pad is moistened by urine (see N. H. Azrin, T. J. Sneed and R. M. Foxx, "Dry Bed Training: Rapid Elimination of Childhood Enuresis," *Behavioral Research and Therapy*, vol. 12, pp. 147-156, 1974), it is very likely that aversive conditioning can be used to successfully treat bruxism, which like enuresis occurs during lighter stages of sleep. Based upon the results of the treatment of enuresis, it is likely that an extended arousal period would improve aversive conditioning treatment efficiency for bruxism and reduce relapse rates. Most recent treatment recommendations are that treatments for bruxism include (1) an arousal contingency which, for example, requires the patient to wake up and turn off an alarm, (2) an over-correction procedure, which could be, for example, a positive practice such as massaging tense jaw muscles and relaxing and (3) an intermittent consequence schedule, wherein not all bruxing events trigger the alarm, to wean the patient from the treatment (see M. Cherasia, et al , above).

Several U.S. patents disclose devices for determining masticatory, movements U.S. Pat. No. 3,297,021, entitled "Self-Contained Intra Oral Strain Gauge," to Davis, et al., teaches the use of a strain gage sensor mounted with a radio transmitter in a partial denture (false tooth) to determine the forces between the maxilla and mandible. When the patient bites and puts pressure o the false tooth, the strain gage changes capacitance in a way which is proportional to the pressure exerted. The gage is incorporated in a radio transmitter which transmits a radio signal which is proportional to the pressure on the tooth. In this way, pressure is monitored externally. U.S. Pat. No. 4,355,645, entitled "Device for Displaying Masticatory Muscle Activities," to Mitani, et al., teaches the use of an electrode device to determine activities of the masticatory muscles.

U.S. Pat. Nos. 4,169,473 and 4,304,227, to Samelson, are directed to the treatment of snoring and bruxism. The Samelson devices are molded to the upper and lower dental surfaces. The device's engagement with at least one of the user's dental arches is disclosed to eliminate nocturnal tooth grinding. U.S. Pat. No. 4,114,612, to Benjamin discloses a device for relieving muscular tension of the head-neck region of a user. Since symptoms of head-neck tension are said to induce grinding of the teeth (according to this patent), this device is claimed to treat bruxism. U.S. Pat. No. 4,220,142, to Rosen, is a behavior shaping device for eliminating nocturnal sounds such as snoring. An alarm is activated to wake the user when a predetermined level of sound is sensed. It is said that this device can be used to treat bruxism.

The Snore Suppressor, manufactured by Crossley Electronics in Austin, Tex., is primarily marketed as a treatment for snoring, although the manufacturer purports that it will also cure bruxism and sleep apnea. This device is worn as a collar by the patient. Any sound, such as a snore or a tooth grinding sound, causes a tiny electrical impulse to be applied through electrodes that touch each side of the neck. The electric impulse is set low enough so that it does not disturb the sleeper, but allegedly does train the subconscious mind to eliminate snoring (or bruxism). The manufacturer claims an eighty percent cure rate, although this figure appears to be based upon the number of people returning the device under a money back guarantee.

U.S. Pat. No. 4,669,477, entitled "Apparatus and Method for Preventing Bruxism," to Ober, discloses an apparatus for producing an electrical stimulation signal, attached to a patient's jaw muscle, to cause the jaw to open. The electrodes are positioned to sense an electromyographic (EMG) signal indicative of jaw muscle activity and jaw clenching. When bruxism is detected, an electrical stimulation signal is applied to the jaw muscle, thereby causing the jaw to open. Similar devices, sold under the trademarks J-4 and BNS-40 Myomonitor, are distributed by Myotronics, Inc., of Seattle, Washington. These devices all require the user to wear electrodes attached over the masseter muscles.

SUMMARY OF THE INVENTION

In accordance with the present invention, there is provided an aversive conditioning apparatus fittable into a user's mouth for treating bruxism. The apparatus comprises a mouth guard housing comprising biting surfaces against which the user's teeth are positionable, a switch structure communicating with the biting surfaces, the switch structure being responsive to the user's biting the biting surfaces with force above a predetermined threshold amount, shock delivering electrodes communicating to a preselected portion of the user's mouth for delivering electric shock thereto, and a source of electric current responsive to the switch structure and operably connected to the shock delivering electrodes for providing electric current to the shock delivering electrodes when the switch structure is bitten with force above the predetermined threshold amount by the user. The electric current source preferably comprises a battery and most preferably comprises a rechargeable battery. The switch structure preferably comprises spaced conductive elements which are disposed to be forced together by the user exerting biting force thereon in excess of the predetermined threshold amount. The electric shock is preferably delivered to the user's gums.

The invention also comprises an aversive conditioning apparatus comprising an electric power providing source, a mouth guard housing comprising biting surfaces against which a user's teeth are positionable, a switch structure operably connected to the electric power providing source and communicating with the biting surfaces, the switch structure being responsive to the user's biting the biting surfaces with force above a predetermined threshold amount, means responsive to the switch structure for sensing a selected number of switch actuating biting events within a preselected time interval and for initiating a signal in response thereto, and an alarm responsive to the sensing means for providing an alert to the user when the sensing means provides a signal thereto.

The invention additionally comprises an aversive conditioning strain gage apparatus for treating bruxism, fittable into a user's mouth. This apparatus comprises a mouth guard housing comprising biting surfaces against which the user's teeth are positionable, an electric power source, strain gages operably connected to the power source and communicating with the biting surfaces, the strain gages being responsive to the user's biting the biting surfaces with force above a predetermined threshold amount, and an alarm operably responsive to the strain gage for providing an alert to the user when the strain gage is bitten with force above the predetermined threshold amount by the user. The strain gage preferably comprises strain responsive resistors connected in a Wheatstone bridge configuration.

The invention additionally comprises one or more force sensing devices incorporated into a mouth guard housing for use in detecting bruxism. This apparatus comprises a mouth guard housing comprising biting surfaces against which the user's teeth are positionable, an electric power source, one or more force sensing devices, such as pressure sensing resistors, operably connected to the power source and communicating with the biting surfaces, the force sensing device(s) being responsive to the user's biting the biting surfaces with a force above a predetermined threshold amount.

The alarm of the invention can provide audio, visual, electric shock multi-sensory, or other alert stimulation to the user. The alarm may comprise a radiowave transmitter and receiver. The radiowave receiver may be disposed external to the user's mouth and may be remote and unconnected to the radiowave transmitter. The alarm can receive input from a user to turn it off, such as via a keypad. Means for counting and recording the number of bruxing events occurring over a determined time period can be provided; and when the alarm is to be initiated and the number of times the alarm can be initiated over a determined time period can be controlled.

One object of the present invention is to provide treatment and a cure for bruxism.

Another object of the present invention is to utilize aversive conditioning for treating diurnal and nocturnal bruxism.

One advantage of the present invention is that a user can use an apparatus in accordance therewith for self treatment.

Another object of the present invention is that an apparatus in accordance therewith can be used safely, is inexpensive to manufacture and use, and is easy to learn to use.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

BRIEF DESCRIPTION OF THE DRAWINGS

The accompanying drawings, which are incorporated into and form a part of the specification, illustrate several embodiments of the present invention and, together with the description, serve to explain the principles of the invention.

DETAILED DESCRIPTION OF THE INVENTION

Figure 1:
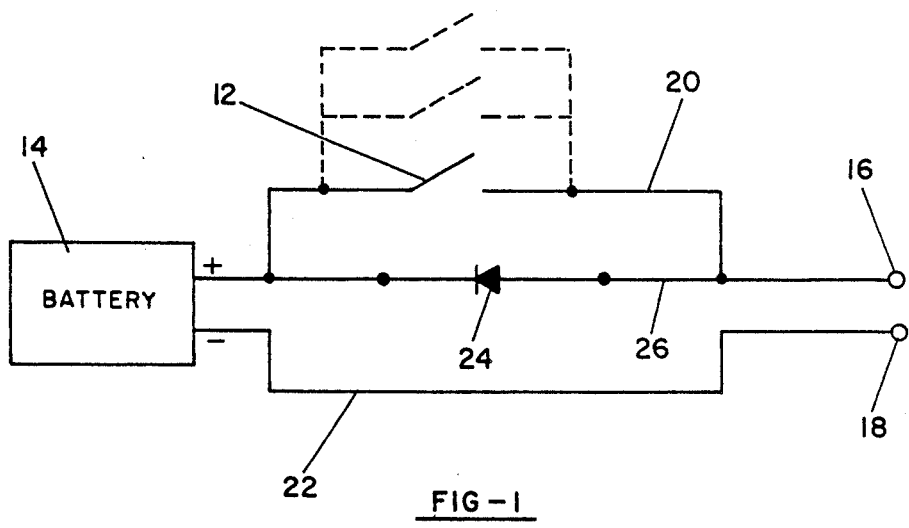
FIG. 1 schematically illustrates a preferred embodiment of a diurnal splint apparatus in accordance with the invention.

Reference is now made to FIG. 1 which schematically shows a preferred diurnal splint apparatus in accordance with the invention. This embodiment is particularly useful for treating diurnal or daytime bruxism. The diurnal splint of FIG. 1 can be worn by a user throughout the day during periods when the user is reading, studying, or involved in any other day-to-day activities, which can be safely practiced with a mouth guard in place. The diurnal splint apparatus is entirely self-contained and may be held within the mouth without any wires leading from the mouth or external power supply or alarm devices. It is embodied in a hard plastic mouth guard or "splint" (not shown), which is fittable to the mouth of the user.

The preferred diurnal splint apparatus of the invention comprises one or more switches 12 which are disposed on biting surfaces of the mouth guard. The switches 12 are preferably thin and may comprise two conductive grids or two conductors separated by a small air space. When the grids come into contact in response to biting, preferably when the biting is at a force above a predetermined threshold amount, the switch 12 is closed. FIG. 1 simply shows a switch 12 in schematic form. Those skilled in the art will recognize how such switches can be embodied in a mouthpiece or splint and the invention is not limited to any particular switch used. A power source 14 which preferably comprises one or more rechargeable batteries, although it may comprise non-rechargeable batteries, connects to electrodes 16 and 18 through switch 12 on conductive lead line 20 to electrode 16 and through lead line 22 to electrode 18. A diode 24 on line 26 is provided so that electric current can flow from lead 16 into battery 14 during recharging, but the battery 14 is prevented from discharging therethrough while in use. Electrodes 16 and 18 are disposed on the mouth guard or splint to contact, for example, the gumline of the user. When switch 12 is closed by the bruxing event, electrodes 16 and 18 electrically shock the user at the gumline to make him aware of his bruxing behavior. The batteries are recharged periodically, perhaps each night, by removing the splint from the mouth and applying voltage across terminals 16 and 18. In the preferred embodiment, the battery pack 14 supplies a voltage of 4.8 volts which provides sufficient shock to make a user aware of the bruxing. This is achieved by placing four 1.2 volt watch-size batteries in series in power source 14.

Figure 2:
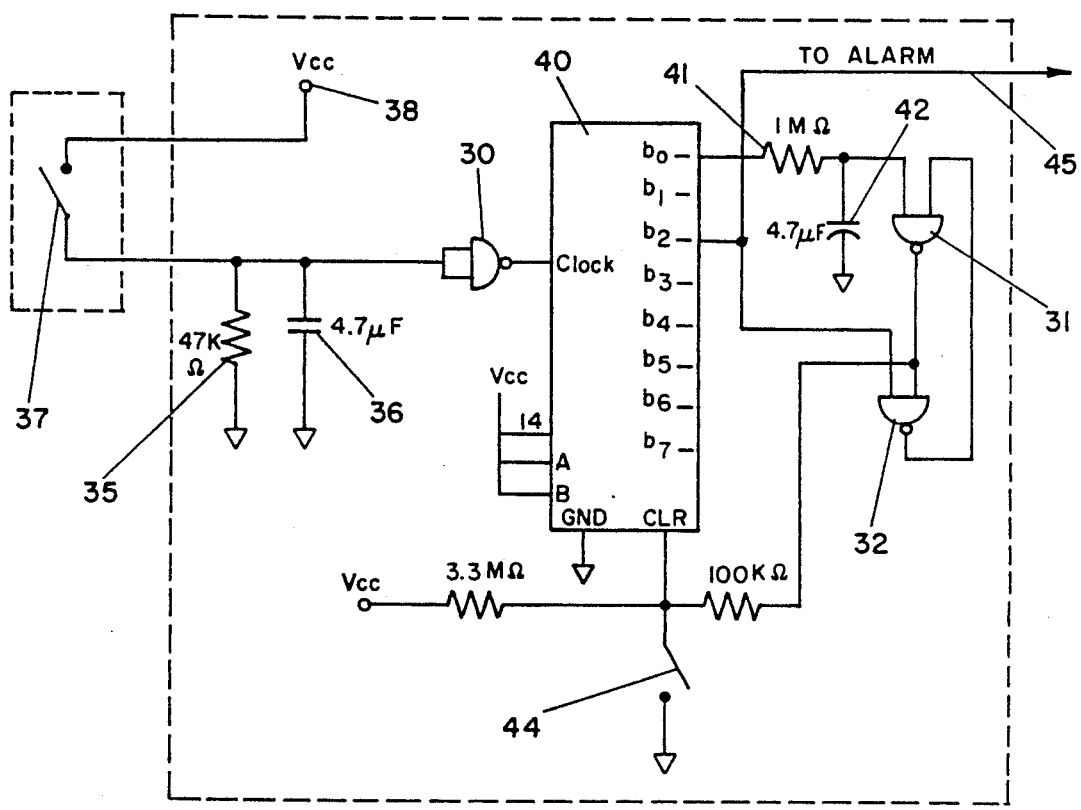
FIG. 2 schematically shows a nocturnal aversive conditioning apparatus in accordance with the invention.

Reference is now made to FIG. 2 which shows a preferred apparatus particularly adapted for use at night for aversive conditioning in the treatment of bruxism. The FIG. 2 apparatus also comprises a mouth guard having embedded switches that are normally open, but which close when bitten. The mouth guard may be quite similar in appearance to the one of FIG. 1, but unlike the diurnal splint of FIG. 1, all the batteries and electronic sensing components are housed externally to the user's mouth and are connected to the mouthpiece switch through thin wires coming out of the mouth.

FIG. 2 illustrates Nand gates 30, 31, and 32, which are, in the preferred embodiment, Schmidt triggered CMOS type CD4093 or 74C132 devices. A resistor 35 and capacitor 36, together with Nand gate 30 ensure that a switch 37 is debounced, i.e., that a single pressing of switch 37 is not detected as multiple switchings. When switch 37 is closed, capacitor 36 charges to an initial voltage, preferably 3.6 volts, through the internal resistance of the battery power supply from source 38. When switch 37 is open, capacitor 36 discharges through resistor 35 and the input of gate 30 continues to see a high signal until capacitor 36 discharges. If a second closing of switch 37 occurs soon after the first closing, it does not affect gate 30, since the input thereto is still at a high voltage level. The output of gate 30 is to a clock input (e.g., a 74C164 CMOS serial to parallel shift register 40). Initially, when cleared, register 40 has a zero level on all output lines $b_0$–$b_7$. When a low to high transition occurs at the clock due to the closing of switch 37 in the mouthpiece, $b_0$ goes to a high level. This output will stay high thereafter until the register 40 is cleared. When $b_0$ first goes to a high level, resistor 41 and capacitor 42 serve to hold the input to gate 31 low for a period of time (e.g., five seconds). If the input to gate 31 goes to a high level before two more clock triggers occur due to closings of switch 37, the output of gate 31 goes to a low level resetting the register 40. Upon reset, $b_0$–$b_7$ go to a low level and this makes the output of gate 31 at a high level, enabling the register 40 once again. On the other hand, if a total of three or more clock triggers have been received at the register 40 at the time that the input to gate 31 goes to a high level, $b_2$ will remain at a high level and no reset will occur. To trigger an alarm (not shown in FIG. 2), $b_2$ may be utilized. The alarm can be turned off only manually, using switch 44 to reset the register 40. The alarm may be as shown in FIG. 3.

In accordance with the preferred invention, triggering the alarm by swallowing or briefly touching the teeth together is prevented from occurring. The alarm is triggered only after a determined number of mouth piece switch closings occur within a specified time period, such as a five second interval, using the preferred embodiment of the invention. Those skilled in the art will appreciate that five or more mouthpiece closings within a seven second interval or other number of closings within another selected time interval can be used to initiate the alarm and that the preferred embodiment's three closings in a five second period are for purposes of illustration only. For example, four or more closings could be used to trigger the alarm using $b_3$ instead of $b_2$, five or more by using $b_4$, and so on. The five second monitoring interval can be lengthened by increasing the resistance of resistor 41, which is one MΩ in the preferred embodiment, or by increasing the capacitance of capacitor 42, which is 4.7 μF in the preferred embodiment. The time interval can be shortened by decreasing the resistance of resistor 41 or the capacitance of capacitor 42.

Electronic sensing circuitry of the FIG. 2 embodiment may be housed in a very small package external to the mouth. This package can also be used to house the power supply, such as three 1.2 volt batteries in the alarm of FIG. 3 hereinafter described. It can be located, for example, as a hearing aid type of device, placed behind the ear. It can also be disposed in a headband or clipped to clothing such as pajamas.

Figure 3:
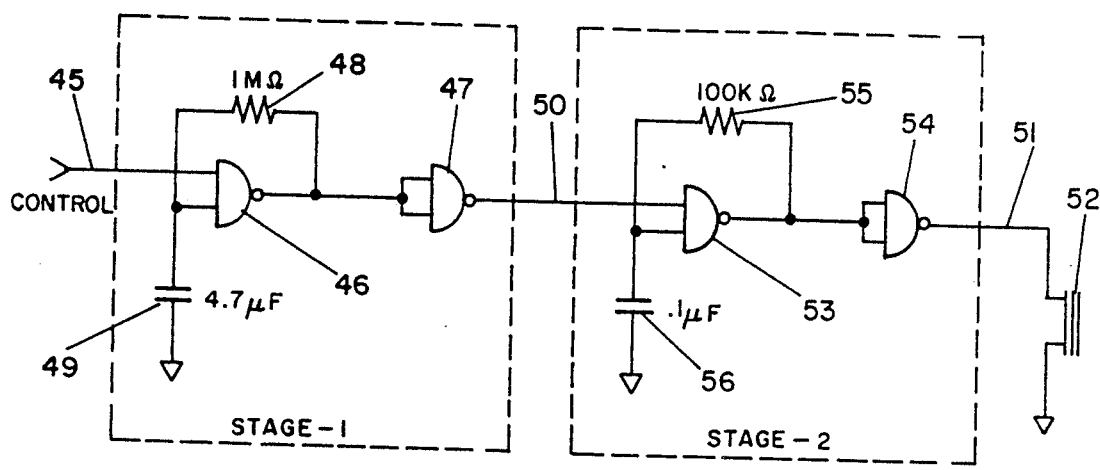
FIG. 3 shows a simple piezobuzzer for use with the FIG. 2 embodiment.

An alarm useful with the FIG. 2 embodiment is shown in FIG. 3, which illustrates a simple piezoelectric buzzer circuit. When the control line 45 outputting from the FIG. 2 embodiment into FIG. 3 is at a high level, stage 1 generates a square wave of approximately 3 Hz frequency. Stage 1 comprises Nand gates 46 and 47, resistor 48 and capacitor 49. The square wave generated by stage 1 on output line 50 enables and disables stage 2, which generates a square wave of approximately 1 kHz frequency on output line 51 to a buzzer 52. Stage 2 comprises Nand gates 53 and 54, resistor 55, and capacitor 56. Thus, in the preferred embodiment, as illustrated in FIG. 3, the buzzer 52 will buzz with a pulsating 1 kHz buzz. This type of a pulsating noise is known to be particularly effective for arousing a sleeper; it is much more annoying than a constant 1 kHz buzz would be and is therefore utilized on many electronic alarm clocks.

Instead of using an alarm which is connected to the mouth guard switch via wires coming out of the mouth, the alarm control output line 45 from FIG. 2 could be used to control a radiowave transmitter within the mouth guard to communicate with a detached or unconnected external alarm. The external alarm could be located, for example, across the room on a night stand or dresser and could be powered from a wall socket. This alarm need not be compact. This external alarm unit could include an audio alarm, a visual alarm, such as turning on or flashing the bedroom lights, or other alarm means. The alarm can use multiple stimuli, for example, to cause a maximum arousal and require the bruxist to arise and cross the room to turn the unit off. Requiring the patient to wake up and turn off the alarm would be the type of arousal contingency thought by some to be necessary for the successful treatment of bruxism. The alarm unit could also incorporate a keypad requiring the bruxist to be awake enough to punch in a certain sequence of keys in order to discontinue the alert or turn the unit off. The apparatus can incorporate a counter to keep track of the number of bruxing events occurring during a night so that improvement could be gaged over time. The apparatus could be programmed to ignore preset percentages of bruxing events, thus implementing an intermittent consequences schedule, which again is thought to be conducive to the treatment of bruxism. By practicing an overcorrection procedure, such as massaging tense jaw muscles upon awakening, a patient would have all of the elements thought necessary for a multi-faceted approach to treatment using aversive conditioning.

Figure 4:
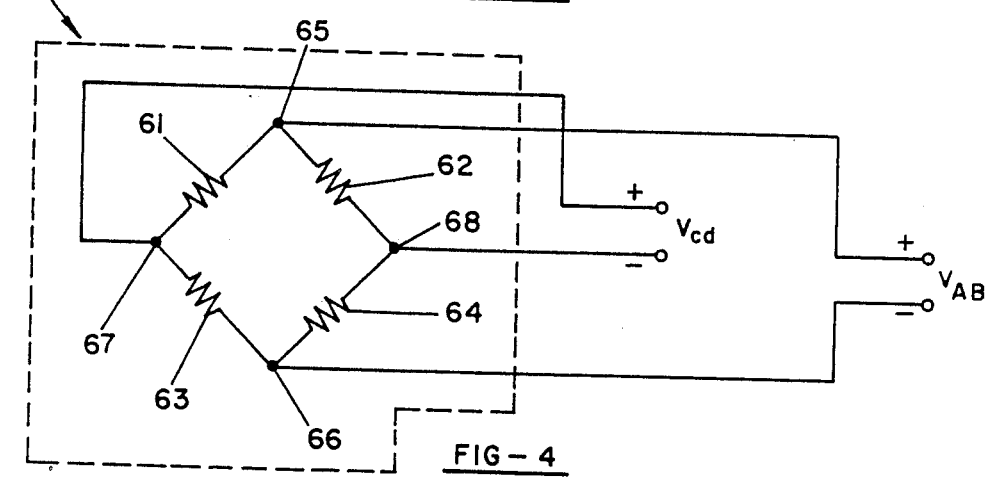
FIG. 4 illustrates an aversive conditioning apparatus in accordance with the invention utilizing strain gages connected in a Wheatstone bridge configuration.
Figure 5:
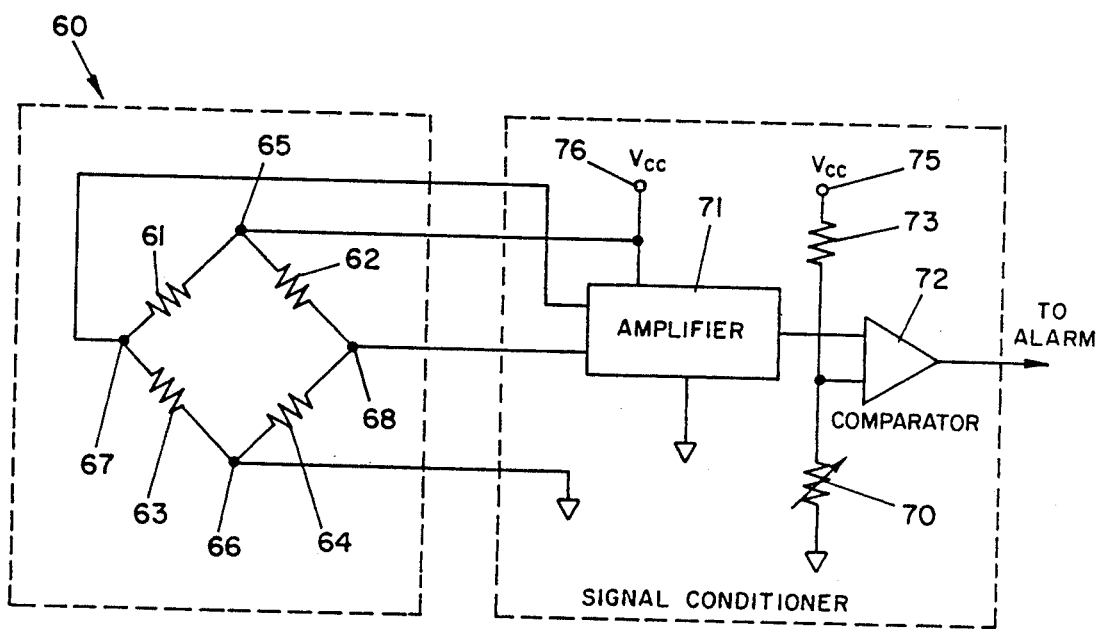
FIG. 5 illustrates an electrical schematic for the strain gage aversive conditioner utilizing the strain gage Wheatstone bridge of FIG. 4.

Another embodiment of the invention is illustrated in FIGS. 4 and 5. In this embodiment, a strain sensor 60 comprising four resistive strain gages 61, 62, 63, and 64, arranged in a Wheatstone bridge, is incorporated into a mouthpiece instead of a switch. The strain sensor 60 is responsive to the user's biting. As is well known in a resistance type strain gage, a wire is bonded to the material in which strain is to be assessed, and electrical resistance in the wires is proportional to the length and width of the wire. When the material under stress deforms, the strain gage also deforms, which changes its resistivity. Resistors 61, 62, 63, and 64 are mounted in four different locations in the mouthpiece and a constant voltage is applied between terminals 65 and 66. If resistors 61, 62, 63, and 64 are identical in resistance value, the voltages between nodes 67 and 68 are zero. Under strain, the resistors become nonidentical and the voltage across terminals 67 and 68 becomes nonzero. Therefore, the voltage across terminals 67 and 68 reflects strain to the material and indicates grinding, clenching, or biting by the wearer of the mouthpiece. Voltage will always be small in value since changes in strain gage resistance are always small and must be amplified. When the amplified signal exceeds some preset threshold, an alarm signal is triggered. The alarm can be an audio alarm, or a radio signal could be transmitted to a remote location, such as a night stand unit, as discussed with reference to FIGS. 2 and 3.

FIG. 5 schematically illustrates a strain gage aversive conditioner using the strain gage Wheatstone bridge of FIG. 4. As seen therein, resistor 70 is a variable resistor that can be used to set the trigger threshold. It is preferably set so that heavy biting triggers the alarm, whereas swallowing or light biting will not. The signal conditioner as seen in FIG. 5 comprises an amplifier 71 and comparator 72. Resistor 73 connects to comparator 72 from voltage source 75. Voltage source 76 is applied to amplifier 71 and across the Wheatstone bridge. This embodiment is particularly advantageous in that the strain gages may be embedded in the splint. Their placement is not critical and because they are embedded, leakage problems, such as saliva shorts, can be avoided. Too, teeth clenching will trigger the alarm and multiple contacts within a specified period of time are not required. Debounce circuitry is not needed because any biting of sufficient force will trigger the alarm. Thus, this device is actuated more by the amount of force exerted by the biting and teeth clenching than by the number of biting or clenching episodes occurring within a predetermined period of time.

Figure 6:
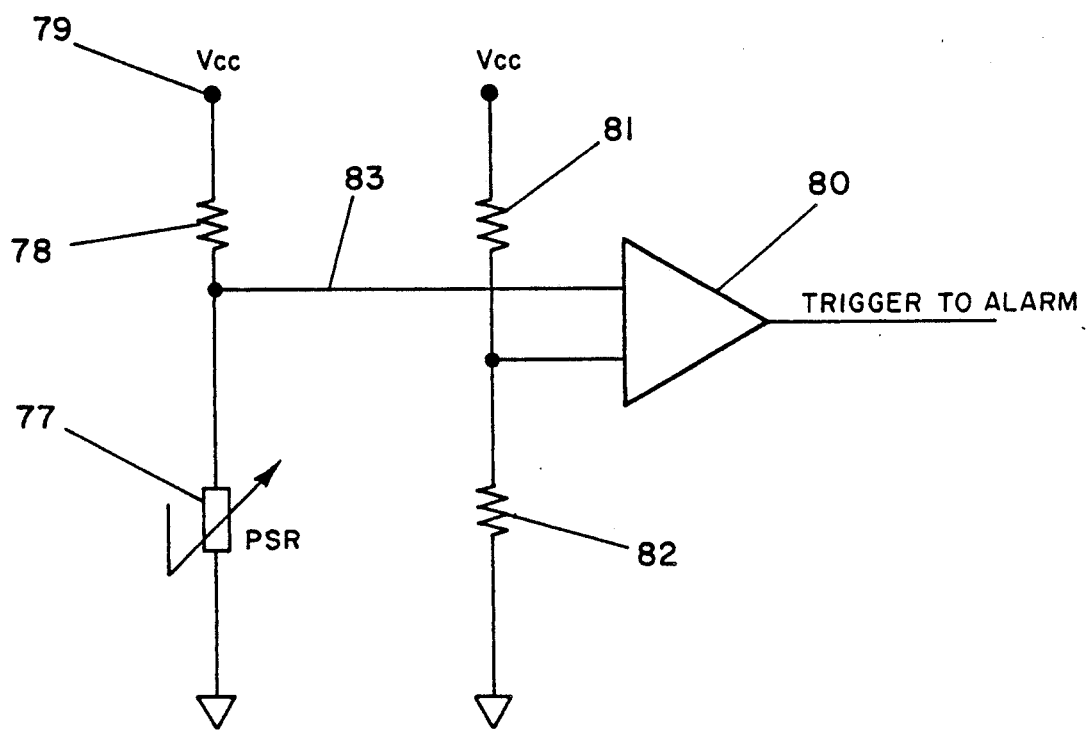
FIG. 6 illustrates an electrical schematic for sensing bruxing behavior using a pressure sensing resistor incorporated into a mouth guard.

Another embodiment of the invention is illustrated in FIG. 6. In this embodiment, at least one pressure sensing resistor (PSR) is used to detect bruxing events. A PSR is a thick film force sensor, the resistance of which decreases as a function of applied force. The change in resistance as a function of applied force is much greater with a PSR than with a conventional resistive strain gage. Consequently, a bridge and amplifier are not required. In addition, a PSR has a time constant of several milliseconds so that the switch debounce circuitry is not needed.

FIG. 6 schematically illustrates an aversive conditioner utilizing a PSR 77 which is placed within a mouth guard so as to be responsive to biting force. A resistor 78 connects to PSR 77 from a voltage source 79 and forms a voltage divider with PSR 77. A comparator 80 whose threshold voltage is set by the voltage divider using resistors 81 and 82 is used to set off an alarm when the voltage on line 83 falls below the threshold value. The trigger can be connected to an audio alarm via wires coming out of the mouth or could be used to send a radio signal (via a radio transmitter within the mouth guard) to a receiver/alarm at a remote location as discussed with reference to FIGS. 2 and 3.

By experimentation, a user will determine which embodiment will be most useful.

Although the invention has been described with reference to these preferred embodiments, other embodiments can achieve the same results. Variations and modifications of the present invention will be obvious to those skilled in the art and it is intended to cover in the appended claims all such modifications and equivalents.

What is claimed is:

1. An aversive conditioning apparatus completely fittable into a user's mouth for treating both diurnal and nocturnal bruxism, said apparatus comprising:
   a mouth guard housing comprising biting surfaces against which the user's teeth are positionable;
   switch means communicating with said biting surfaces, said switch means being responsive to the user's biting said biting surfaces with force above a predetermined threshold amount, and to the cessation of the user's biting;
   shock delivering electrode means communicating to a preselected portion of the user's mouth for delivering electric shock thereto, said electric shock being sufficient to consciously shock and alert the user when the user bites said biting surfaces with force above said predetermined threshold amount; and
   means responsive to said switch means and operably connected to said shock delivering electrode means for providing electric current to said shock delivering electrode means only when said switch means is bitten with force above said predetermined threshold amount by user and for stopping said electric current to said shock delivering electrode means when the user ceases biting.

2. The invention of claim 1 wherein said electric current providing means comprises battery means.

3. The invention of claim 2 wherein said battery means comprises rechargeable battery means.

4. The invention of claim 1 wherein said switch means comprises spaced conductive elements which are disposed to be forced together by the user exerting biting force thereon in excess of said predetermined threshold amount.

5. The invention of claim 1 wherein said preselected portion of the user's mouth for delivering electric shock thereto is the user's gums or cheeks.

6. An aversive conditioning apparatus completely fittable into a user's mouth for treating both diurnal and nocturnal bruxism, said apparatus comprising:
   means for providing electric power;
   a mouth guard housing comprising biting surfaces against which a user's teeth are positionable;
   switch means operably connected to said electric power providing means and communicating with said biting surfaces, said switch means being responsive to the user's biting said biting surfaces with force above a predetermined threshold amount;
   means responsive to said switch means for sensing a selected number of switch actuating biting events within a preselected time interval and for initiating a signal in response thereto;
   alarm means responsive to said sensing means for providing an alert to the user when said sensing means provides said signal in response thereto.

7. The invention of claim 6 wherein said alarm means comprises means for providing an audio alert to the user.

8. The invention of claim 6 wherein said alarm means comprises radiowave transmitter means disposed within said mouth guard housing and means for transmitting radiowaves from said radiowave transmitter means to a radiowave receiving and alarm producing device external to the user's mouth.

9. The invention of claim 8 wherein said external radiowave receiving and alarm producing device is physically remote from and unconnected to said radiowave transmitter means.

10. The invention of claim 6 wherein said alarm means provides at least one alert selected from the group consisting of audio, visual, and electric shock to the user.

11. The invention of claim 6 wherein said alarm means comprises means for providing multi-sensory stimulation to the user.

12. The invention of claim 6 wherein said alarm means further comprises means for receiving input from the user to discontinue said alert.

13. The invention of claim 12 wherein said input receiving means comprises keypad means whereby the user must punch in a predetermined sequence of keys to discontinue said alert.

14. The invention of claim 6 comprising means for the user to program said apparatus to ignore a preselected number of bruxing events before said alarm means is enabled.

15. The invention of claim 6 further comprising means for counting and recording a number of bruxing events occurring over a determined time period.

16. The invention of claim 6 further comprising means for controlling the number of times said alarm means can be initiated over a determined time period 17. An aversive conditioning strain gage apparatus for treating bruxism, completely fittable into a user's mouth for treating both diurnal and nocturnal bruxism, and apparatus comprising:
   a mouth guard housing comprising biting surfaces against which the user's teeth are positionable;
   electric power means;
   strain gage means operably connected to said electric power means and communicating with said biting surfaces, said strain gage means being responsive to the user's biting said biting surfaces with force above a predetermined threshold amount; and
   alarm means operably responsive to said strain gage means for providing an alert to the user when said strain gage means is bitten with force above said predetermined threshold amount by the user.

18. The invention of claim 17 wherein said alarm means comprises radiowave transmitter means disposed within said mouth guard housing and means for transmitting radiowaves from said radiowave transmitter means to a radiowave receiving and alarm producing device external to the user's mouth.

19. The invention of claim 18 wherein said external radiowave receiving and alarm producing device is physically remote from and unconnected to said radiowave transmitter means.

20. The invention of claim 17 wherein said alarm producing means provides at least one alert selected from the group consisting of audio, visual, and electric shock to the user.

21. The invention of claim 17 wherein said alarm means further comprises means for receiving input from the user to discontinue said alert.

22. The invention of claim 17 comprising means for the user to program said apparatus to ignore a preselected number of bruxing events before said alarm means is enabled.

23. The invention of claim 17 wherein said strain gage means comprises resistive strain gages connected in a Wheatstone bridge.

24. The invention of claim 17 comprising a variable resistor for setting the predetermined threshold amount.

25. The invention of claim 17 wherein said strain gage means are disposed within said mouth guard housing.

26. An aversive conditioning apparatus completely fittable into a user's mouth for treating both diurnal and nocturnal bruxism, said apparatus comprising:
 a mouth guard housing comprising biting surfaces against which a user's teeth are positionable;
 electric power means;
 force sensing means comprising thick film means operably connected to said electric power means and communicating with said biting surfaces, said force sensing means comprising an electrical resistance being responsive to force applied to said biting surfaces by the user biting on said biting surfaces; and
 means for comparing said electrical resistance of said force sensing means with a predetermined electrical resistance value, said predetermined electrical resistance value being low enough to respond to both diurnal and nocturnal bruxism; and
 means for setting off an alarm means when said electrical resistance of said force sensing means reaches said predetermined electrical resistance value, when force is applied by the user to said biting surfaces.

27. The invention of claim 26 wherein said force sensing means comprises at least one pressure sensing resistor.

28. The invention of claim 27 wherein said pressure sensing resistor decreases in resistance as force applied thereto increases.

29. The invention of claim 26 wherein said alarm means comprises radiowave transmitter means disposed within said mouth guard housing and means for transmitting radiowaves from said radiowave transmitter means to a radiowave receiving and alarm producing device external to the user's mouth.

30. The invention of claim 29 wherein said external radiowave receiving and alarm producing device is physically remote from and unconnected to said radiowave transmitter means.

31. The invention of claim 26 wherein said alarm producing means provides at least one alert selected from the group consisting of audio, visual, and electric shock to the user.

32. The invention of claim 26 wherein said alarm means further comprises means for receiving input from the user to discontinue an alert provided by said alarm means.

33. The invention of claim 26 comprising means for the user to program said apparatus to ignore a preselected number of bruxing events before said alarm means is enabled.

* * * * *